United States Patent [19]

Crisp

[11] Patent Number: 5,178,837
[45] Date of Patent: Jan. 12, 1993

[54] ROCK ANALYZER

[75] Inventor: Russell I. Crisp, Walton-on-Thames, England

[73] Assignee: The British Petroleum Company p.l.c., London, England

[21] Appl. No.: 590,045

[22] Filed: Sep. 27, 1990

Related U.S. Application Data

[63] Continuation of Ser. No. 356,629, May 22, 1989, abandoned, which is a continuation of Ser. No. 147,026, Jan. 19, 1988, abandoned, which is a continuation of Ser. No. 888,009, Jul. 22, 1986, abandoned.

[30] Foreign Application Priority Data

Jul. 25, 1985 [GB] United Kingdom ............... 8518821

[51] Int. Cl.$^5$ ........................................ G01N 31/12
[52] U.S. Cl. ........................................ 422/78; 422/80; 422/157
[58] Field of Search ........................ 422/78, 80, 157; 436/31, 32, 141, 155

[56] References Cited

U.S. PATENT DOCUMENTS

| | | | |
|---|---|---|---|
| 3,572,092 | 3/1971 | Zernow | 422/78 |
| 3,788,124 | 1/1974 | Teton | 436/1 |
| 3,861,875 | 1/1975 | Joslyn | 422/28 |
| 3,982,893 | 9/1976 | Joslyn | 422/28 |
| 4,151,060 | 4/1979 | Isenberg | 55/158 |
| 4,153,415 | 5/1979 | Espitalie et al. | 436/31 |
| 4,229,181 | 11/1980 | Espitalie et al. | 436/31 |
| 4,485,071 | 11/1984 | Larter | 422/78 |

FOREIGN PATENT DOCUMENTS 1320954 6/1973 United Kingdom ................ 422/30

OTHER PUBLICATIONS

Websters 9th New Collegiate Dictionary, Merriam-Webster, Mass., 1985, p. 916.

Primary Examiner—Thi Dang
Attorney, Agent, or Firm—Morgan & Finnegan

[57] ABSTRACT

A rock analyser includes a chamber containing a heater (2) and the sensor (6) of a hydrocarbon detector (7), the heater (2) being connectable to a source of power (5) and the sensor (6) being connected to the remainder of the hydrocarbon detector (7). The analyser determines the amount of hydrocarbon material present in the rock. It is portable and is useful for field screening tests to reduce the number of samples sent for laboratory analysis.

4 Claims, 1 Drawing Sheet

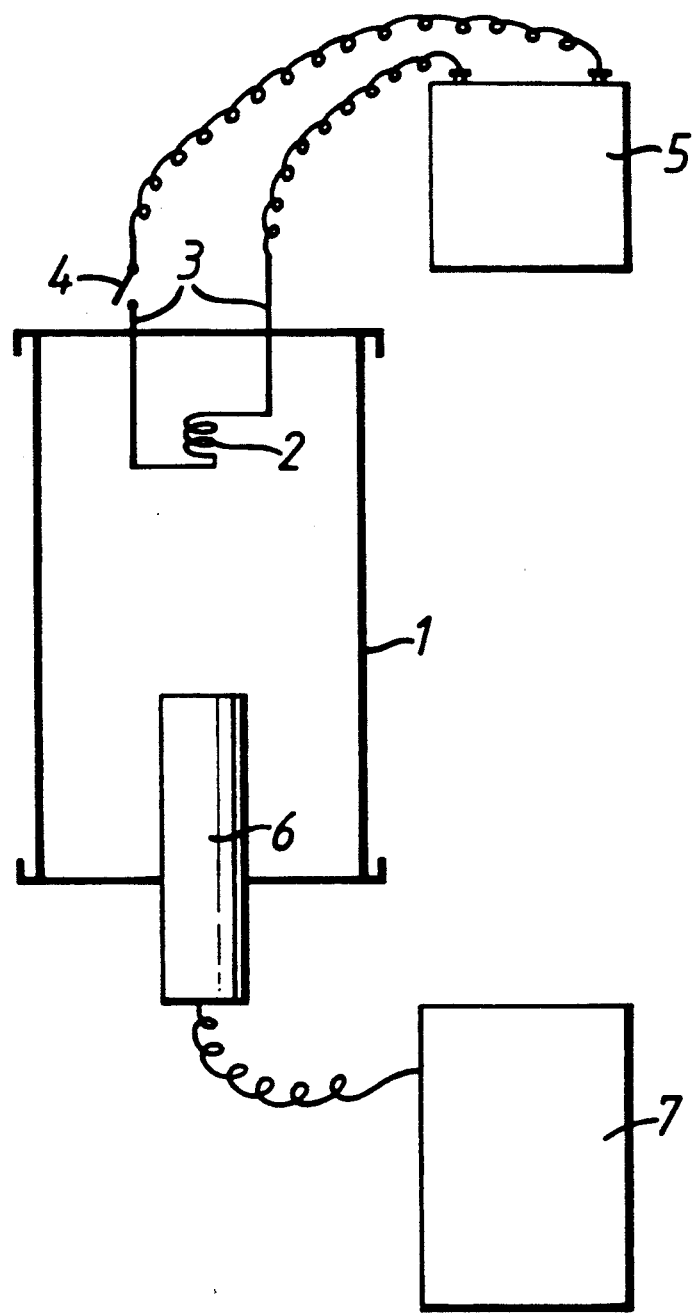

ROCK ANALYZER

This is a continuation of co-pending application Ser. No. 07/356,629 filed on May 22, 1989 (now abandoned) which is a continuation of Ser. No. 07/147,026 filed on Jan. 19, 1988, (now abandoned), which is a continuation of 06/888,009 filed Jul. 22, 1986, (abandoned).

This invention relates to a portable rock analyser.

Organic geochemists routinely measure the organic content of rocks by laboratory pyrolysis. This organic matter may be divided into two types; volatile material (oil) and polymeric, involatile material (kerogen). On heating, kerogen decomposes to give volatile components (oil and gas) and an inert residue. Thus rocks containing significant quantities of labile kerogen are considered to be hydrocarbon source rocks. Conventional laboratory procedure for identifying source rocks includes a two-stage pyrolysis in an inert atmosphere with the expelled hydrocarbons being detected by a flame ionisation detector (FID). The first stage of the pyrolysis takes place between 250° and 300° C. and is intended to detect only the oil. The second stage occurs at 500°–600° C., at which temperatures kerogen breakdown rapidly occurs. The two values obtained are referred to as S1 or P1 (low temperature products) and S2 or P2 (high temperature products). The units are usually kg (hydrocarbons) per tonne (rock). A typical laboratory determination takes 20–30 minutes and uses carefully prepared and finely ground rock samples.

Considerable effort is spent performing a great many of these analyses as a means of identifying rich samples, suitable for further geochemical analysis. The majority of samples tested contain little or no organic material, however.

It is an object of the present invention to provide a portable rock analyser for use in field screening tests to reduce the number of worthless samples sent to laboratories for analysis. This will, in turn, allow more expedient analyses of the richer samples.

Thus according to the present invention, there is provided a rock analyser comprising a chamber containing a heater and the sensor of a hydrocarbon detector, the heater being connectable to a source of power and the sensor being connected to the remainder of the hydrocarbon detector.

Hydrocarbon detectors are commercially available. Suitable models include the GL-10 detector for methane manufactured by Molecular Controls Ltd of Leeds, England and the AG 5100 detector for methane, manufactured by International Sensor Technology of California, USA, and described in U.S. Pat. Nos. 3,955,268 and 4,013,943. These are rechargeable battery powered detectors designed for atmospheric monitoring. Whilst the units are primarily designed to detect methane they have been shown to respond to most volatile hydrocarbons. Full Scale Deflection (FSD) corresponds to 5% methane by volume.

The heater may be a ceramic furnace incorporating a heating coil which may be wound from resistance wire and be connectable via a switch to a battery.

The heater may incorporate a timer for better reproducibility.

The heater is heated to a temperature of around 700°–1000° C. in less than 30 seconds when the switch is operated. The temperature and rate of heating are such that an inert atmosphere is not necessary in the pyrolysis chamber to ensure degradation rather than combustion. The volume of the chamber should be such that pyrolysis of a 30 mg sample of rock with a combined hydrocarbon yield (P1+P2) of 50 kg tonne$^{-1}$ would give a theoretical concentration of 5% of hydrocarbons with carbon numbers less than 10 (i.e. full scale deflection). This volume is 100 cm$^3$. Thus the most sensitive range of the instrument is between 1 and 10 kg tonne$^{-1}$ for 30 mg samples.

In practice the range will depend on the actual proportion of the generated hydrocarbon sufficiently volatile to give a detector response, the distribution of these products (since the detector is most sensitive to the lighter hydrocarbons) and the size of the samples tested. The 30 mg sample size is chosen as being a convenient size to handle in the field, without requiring large amounts of power to pyrolyse it.

The instrument is operated by selecting a suitably sized piece of rock, inserting it into the heater and replacing the lid of the cylinder. The power button is depressed for 20–40 seconds and then released. After allowing a further 30–60 seconds for the instrument to stabilise, the detector reading is recorded. The lid is then removed, allowing clean air to purge the detector. The heater can be cleaned by simply depressing the power button for a few seconds. The instrument is then ready to analyse another sample. The whole process takes less than five minutes. Alternatively, the procedure can be automatically controlled by a timer.

BRIEF DESCRIPTION OF THE DRAWING

The invention is illustrated with reference to the accompanying drawing which schematically illustrates an embodiment of the portable rock analyzer of this invention.

The analyser comprises a cylinderical chamber 1 of volume 100 cm$^3$ containing a heating coil 2 wound from four cm of resistance wire (80% Ni, 20% Cr) connected via electrodes 3 and a switch 4 to a two volt lead acid battery 5.

The chamber also contains the sensor 6 of a hydrocarbon detector sold by International Sensor Technology under the reference AG 5100. The sensor 6 is connected to the remainder of the detector 7 which is located outside the chamber 1.

By selecting a suitable cut-off point, below which samples are considered worthless, the instrument can be used to screen samples in the field prior to full geochemical analysis in the laboratory.

This is illustrated by the following examples:

EXAMPLE 1

Pieces of rock of similar size and approximately 30 mg in weight were analysed using the portable instrument described above. A cut-off of 10% FSD was used. All samples were subsequently analysed in the laboratory to check the findings.

The results are presented in Table 1. Samples 1–9 were correctly identified as having little or no hydrocarbon potential. Samples 14–25 were correctly identified as having potentials greater than 1 kg tonne$^{-1}$. Samples 10–13 were identified as having significant potential but were later shown to have little or no potential.

Thus the instrument gives readings which err on the side of caution—in no case was a rich sample mis-identified as being poor. In a real field study this exercise would have saved over one third of the laboratory effort.

TABLE 1

| Sample No | Portable Instrument Reading (% FSD) | Laboratory Pyrolysis Yield (kg tonne$^{-1}$) |
|---|---|---|
| 1 | 4 | 0.3 |
| 2 | 5 | 0.2 |
| 3 | 3 | 0.2 |
| 4 | 3 | 0.1 |
| 5 | 2 | 0 |
| 6 | 2 | 0 |
| 7 | 4 | 0.2 |
| 8 | 1 | 0 |
| 9 | 7 | 0.5 |
| 10 | 18 | 0.8 |
| 11 | 21 | 0.7 |
| 12 | 14 | 0.3 |
| 13 | 17 | 0.8 |
| 14 | 85 | 2.6 |
| 15 | 100 | 4.6 |
| 16 | 53 | 1.7 |
| 17 | 71 | 2.0 |
| 18 | 63 | 2.3 |
| 19 | 63 | 2.2 |
| 20 | 28 | 1.6 |
| 21 | greater than 100 | 10.2 |
| 22 | 65 | 1.9 |
| 23 | 100 | 4.4 |
| 24 | 53 | 1.8 |
| 25 | greater than 100 | 21.0 |

EXAMPLE 2

A further series of tests were carried out in which the detector was fitted with a digital read-out expressed in kg hydrocarbon material per tonne of rock.

The results set out in Table 2 show good agreement between the instrument readings and subsequent analyses carried out under laboratory conditions.

TABLE 2

| Sample No | Portable Instrument Reading (kg/tonne) | Laboratory Pyrolysis Yield (kg/tonne) |
|---|---|---|
| 26 | 30 | 28.0 |
| 27 | 6 | 3.5 |
| 28 | 0.5 | 0.4 |
| 29 | 1.5 | 2.1 |
| 30 | 35 | 17 |
| 31 | 0 | 0 |
| 32 | 2 | 3.3 |
| 33 | 4.5 | 5.8 |
| 34 | 20 | 13.8 |
| 35 | 5 | 8.5 |
| 36 | 16 | 15.8 |
| 37 | 33 | 23.4 |
| 38 | 2 | 2.6 |
| 39 | greater than 50 | 109 |
| 40 | 2 | 2.6 |
| 41 | 34 | 19.4 |
| 42 | 2 | 1.7 |
| 43 | 0.5 | 0 |
| 44 | 0.4 | 0 |
| 45 | greater than 50 | 90.2 |
| 46 | 1 | 1.6 |
| 47 | 1.5 | 0.6 |
| 48 | 50 | 68.3 |
| 49 | greater than 50 | 97.4 |
| 50 | 0.6 | 0.2 |
| 51 | 8 | 9.5 |
| 52 | 35 | 28 |
| 53 | 46 | 43.6 |
| 54 | 38 | 48 |
| 55 | 31 | 18 |
| 56 | 1.5 | 2 |
| 57 | 2 | 2 |

I claim:

1. A portable analyzer for determining the amount of hydrocarbons present in a rock comprising:

a chamber for holding a rock sample to be analyzed;

heating means within said chamber for heating the rock sample so as to drive off, without combusting, hydrocarbonaceous material present within the rock sample, said heating means having contact means for electrically connecting said heating means to a source of power;

detecting means for detecting the amount of hydrocarbonaceous material driven off from the rock sample by the heating means, said detecting means comprising sensing means within the chamber and recording means outside the chamber electrically connected to the sensing means.

2. An analyzer according to claim 1 wherein the heating means comprises a ceramic furnace having a heating coil.

3. An analyzer according to claim 2 wherein the heating coil is fabricated from electrical resistance wire and wherein the source of power is an electrical battery.

4. An analyzer according to claim 1 wherein the detecting means is a methane detector.

* * * * *